US012773575B2

(12) United States Patent
Santhanam et al.

(10) Patent No.: US 12,773,575 B2
(45) Date of Patent: Oct. 27, 2026

(54) ARTIFICIAL INTELLIGENCE GUIDED PREDICTION OF SYSTEMATIC CHANGES IN RADIOTHERAPY

(71) Applicant: Siemens Healthineers International AG, Steinhausen (CH)

(72) Inventors: Anand Santhanam, Monmouth Junction, NJ (US); Florin-Cristian Ghesu, Baiersdorf (DE); Yue Zhang, Jersey City, NJ (US)

(73) Assignee: Siemens Healthineers International AG, Steinhausen (CH)

( * ) Notice: Subject to any disclaimer, the term of this patent is extended or adjusted under 35 U.S.C. 154(b) by 95 days.

(21) Appl. No.: 18/819,909

(22) Filed: Aug. 29, 2024

(65) Prior Publication Data

US 2026/0061221 A1 Mar. 5, 2026

(51) Int. Cl.
*A61N 5/10* (2006.01)

(52) U.S. Cl.
CPC ......... *A61N 5/1031* (2013.01); *A61N 5/1038* (2013.01); *A61N 2005/1041* (2013.01)

(58) Field of Classification Search
CPC ................ A61N 5/1031; A61N 5/1038; A61N 2005/1041
See application file for complete search history.

(56) References Cited

U.S. PATENT DOCUMENTS

2012/0245453 A1 9/2012 Tryggestad et al.
2020/0360731 A1* 11/2020 Tilly ...................... G16H 30/40
2021/0251516 A1 8/2021 Pai et al.

FOREIGN PATENT DOCUMENTS

WO WO-2017089097 A1 * 6/2017 ........... A61N 5/1038

* cited by examiner

*Primary Examiner* — Mark R Gaworecki
(74) *Attorney, Agent, or Firm* — Foley & Lardner LLP

(57) ABSTRACT

Disclosed herein are methods and systems using artificial intelligence models to predict systematic changes in radiation therapy. The system can generate a first radiotherapy treatment plan using a first medical image depicting at least an anatomical region of a patient. After at least one treatment fraction has been implemented, the system can acquire a second medical image depicting the anatomical region. The system can execute a computer model to compare the first medical image with the second medical image. After at least one subsequent treatment fraction, the system can acquire a third medical image and compare the first medical image with the third medical image. The system can execute, using the medical images, a machine learning model to predict anatomical changes to at least one structure of the patient for the forecasted treatment fraction. The system can transmit the predictions to a radiotherapy treatment planning computer model.

20 Claims, 4 Drawing Sheets

ARTIFICIAL INTELLIGENCE GUIDED PREDICTION OF SYSTEMATIC CHANGES IN RADIOTHERAPY

TECHNICAL FIELD

This application relates generally to generating, training, and operating artificial intelligence (AI) computer models for the prediction of systematic changes in radiation therapy.

BACKGROUND

Radiation therapy (radiation-based therapy or radiotherapy) is a cancer treatment wherein high doses of radiation can kill cancerous cells. The target region of a patient's body that is intended to receive radiation (e.g., a tumor) is referred to as the planning target volume (PTV). The goal is to deliver enough radiation to the PTV to kill the cancerous cells (also referred to herein as a treatment plan or radiation therapy treatment). However, other organs or anatomical regions that are adjacent to or surrounding the PTV can be in the path of radiation beams and can receive enough radiation to be damaged or harmed. These organs, or anatomical regions, are referred to as organs at risk (OARs). Usually, a physician or a radiologist identifies both the PTV and the OARs before planning a treatment plan.

SUMMARY

Radiotherapy (RT) is an important step in treating cancer, particularly for patients with inoperable tumors, where the treatment involves prescribed radiation doses delivered over multiple days or treatment fractions. In this regard, accuracy is crucial, as failing to administer enough radiation to the tumor may result in treatment failure, whereas excessive radiation to the surrounding organs can lead to severe side effects. Image-guided radiotherapy (IGRT), using daily imaging techniques, has advanced treatment precision by verifying patient setup before each treatment fraction. However, patients undergoing radiotherapy often experience physiological regression, such as significant weight loss and tumor shrinkage, which can subtly alter patient anatomy and shift or move the planned target volume (PTV) and organs at risk (OARs) relative to their initial positions. These systematic changes can lead to shifts in patient anatomy, resulting in the underdosing of the PTV and the overdosing of OARs. Since the tumors and the surrounding organs can deform, the patient's positioning can also lead to the underdosing of the tumor and the overdosing of the surrounding organs. These positioning errors, combined with physiological regression, can complicate treatment accuracy.

To maintain therapeutic effectiveness and minimize side effects, frequent updates to the radiotherapy treatment plan (RTTP) are necessary to account for any anatomical changes during the course of treatment. However, the IGRT or treatment planning systems lack the ability to provide periodic replanning, requiring them to undergo a complex procedure. For instance, replanning involves time-consuming steps such as rescheduling CT scans, recontouring structures, developing new treatment plans, and conducting extensive quality assurance checks. This multi-step process can significantly delay treatment delivery, impacting patient care and workflow efficiency in high-volume clinics where maintaining treatment continuity is important.

Furthermore, RTTP creation is typically based on the optimization of certain dosimetric parameters, such as "target coverage," "max dose in the spinal cord," and/or "mean dose in the parotid gland." The used dosimetric parameters and the desired goal values are often based on previously performed outcome studies where there is a correlation between these dosimetric parameters and certain clinical endpoints. The observed correlation between dose distribution and clinical outcomes is sometimes referred to as the "clinical models." Conventional plan optimizers may optimize the RTTP against a given clinical model by defining the desired objectives, but they are bound to use certain generic dosimetric parameters, which were implemented and sometimes hardcoded within the software algorithm during the product development (such as "Dose-to-Volume," "Volume-to-Dose," and/or "Generalized Equivalent Uniform Dose." This static approach is also undesirable because it is time-consuming and computationally intense to revise the software code.

To address the challenges, the technical solutions described herein implement external AI modeling/training techniques that can leverage advancements in AI to predict systematic changes in a patient's anatomy effectively and cost-efficiently, thereby providing dynamic and adaptive radiation therapy planning. In this regard, the technical solutions can use a convolutional long short-term memory (LSTM) architecture, which can integrate the strengths of time series processing with computer vision capabilities. The LSTM model can be suited for applications requiring the prediction of systematic anatomical changes due to its ability to process spatiotemporal data. By introducing convolutional recurrent cells in each LSTM layer, the model can facilitate capturing spatial dependencies, which can be important for modeling the complex relationships between different anatomical structures as they change over time due to radiation therapy. The model's ability to capture spatial relationships can be enhanced by incorporating convolutional layers both in the input-to-state and state-to-state transitions. This dual application of convolutional layers can allow the LSTM model to process and integrate spatial and temporal information, leading to a deeper and more nuanced understanding of how anatomical structures change over time more effectively.

The LSTM model can be structured to operate under a sequence-to-sequence learning framework, where it takes sequences of spatial data (from a series of fraction images) as inputs and predicts sequences representing future anatomical states. This may be accomplished by stacking multiple layers of LSTM cells to form a deep learning model that includes both encoding and forecasting components. The encoding component can capture and condense information from historical anatomical data, while the forecasting component can use the information to predict future changes. This end-to-end trainable model can significantly depart from static approaches that rely on hardcoded dosimetric parameters. As radiotherapy technology progresses, with improvements in imaging technology and the development of more sophisticated machine learning techniques like neural networks, the technical solutions can accommodate various types of spatial functional imaging and more accurately predict spatial changes. The technical solutions can reduce the need for frequent replanning by providing continuous prediction of anatomical changes during the course of radiation therapy, thereby enhancing treatment efficacy and reducing computational costs associated with planning systems.

At least one aspect of the technical solutions is directed to a method of replanning radiotherapy treatment. The method may include generating, by at least one processor, a first radiotherapy treatment plan using a first medical image depicting an anatomical region of a patient, the first radiotherapy treatment plan having a plurality of treatment fractions; after at least one treatment fraction has been implemented, acquiring, by the at least one processor, a second medical image depicting the anatomical region of the patient; executing, by the at least one processor, a computer model to compare the first medical image with the second medical image of the anatomical region of the patient after the at least one treatment fraction; after at least one subsequent treatment fraction has been implemented, acquiring, by the at least one processor, a third medical image depicting the anatomical region of the patient; executing, by the at least one processor, the computer model to compare the first medical image with the third medical image of the anatomical region of the patient after the at least one subsequent treatment fraction; executing, by the at least one processor using the first medical image, the second medical image, and the third medical image, and calculated difference between the first medical image, the second medical image, and the third medical image, a machine learning model to predict anatomical changes to at least one structure of the patient for at least one forecasted treatment fraction; and transmitting, by the at least one processor, the prediction of anatomical changes to a radiotherapy treatment planning computer model, whereby when the radiotherapy treatment planning computer model determines that at least one structure of the patient is being underdosed or overdosed, the radiotherapy treatment planning computer model generates a second radiotherapy treatment plan for the patient.

The artificial intelligence model may be a convolutional long short-term memory model. The artificial intelligence model may be trained on a dataset comprising simulated computed tomography imaging approaches and simulated cone-beam computed tomography imaging approaches for previously treated patients. At least one of the computer model or the machine learning model may further ingest at least one treatment attribute. The machine learning model may further ingest an attribute corresponding to patient positioning. The machine learning model may further ingest an attribute corresponding to a physiological regression. The second radiotherapy treatment plan may include a secondary dose deposition for the at least one structure that is different than a dose deposition of a first dose deposition of the first radiotherapy treatment plan.

At least one aspect of the technical solutions is directed to a system of replanning radiotherapy treatment. The system can include one or more processors configured to: generate a first radiotherapy treatment plan using a first medical image depicting an anatomical region of a patient, the first radiotherapy treatment plan having a plurality of treatment fractions; after at least one treatment fraction has been implemented, acquire a second medical image depicting the anatomical region of the patient; execute a computer model to compare the first medical image with the second medical image of the anatomical region of the patient after the at least one treatment fraction; after at least one subsequent treatment fraction has been implemented, acquire a third medical image depicting the anatomical region of the patient; execute the computer model to compare the first medical image with the third medical image of the anatomical region of the patient after the at least one subsequent treatment fraction; execute, using the first medical image, the second medical image, and the third medical image, and calculated difference between the first medical image, the second medical image, and the third medical image, a machine learning model to predict anatomical changes to at least one structure of the patient for at least one forecasted treatment fraction; and transmit the prediction of anatomical changes to a radiotherapy treatment planning computer model, whereby when the radiotherapy treatment planning computer model determines that at least one structure of the patient is being underdosed or overdosed, the radiotherapy treatment planning computer model generates a second radiotherapy treatment plan for the patient.

The artificial intelligence model may be a convolutional long short-term memory model. The artificial intelligence model may be trained on a dataset comprising simulated computed tomography imaging approaches and simulated cone-beam computed tomography imaging approaches for previously treated patients. At least one of the computer model or the machine learning model may further ingest at least one treatment attribute. The machine learning model may further ingest an attribute corresponding to patient positioning. The machine learning model may further ingest an attribute corresponding to a physiological regression. The second radiotherapy treatment plan may include a secondary dose deposition for the at least one structure that is different than a dose deposition of a first dose deposition of the first radiotherapy treatment plan.

Yet another aspect of the technical solutions is directed to a non-transitory machine-readable storage medium having computer-executable instructions stored thereon that, when executed by one or more processors, cause the one or more processors to: generate a first radiotherapy treatment plan using a first medical image depicting an anatomical region of a patient, the first radiotherapy treatment plan having a plurality of treatment fractions; after at least one treatment fraction has been implemented, acquire a second medical image depicting the at least an anatomical region of the patient; execute a computer model to compare the first medical image with the second medical image of the anatomical region of the patient after the at least one treatment fraction; after at least one subsequent treatment fraction has been implemented, acquire a third medical image depicting the anatomical region of the patient; execute the computer model to compare the first medical image with the third medical image of the anatomical region of the patient after the at least one subsequent treatment fraction; execute, using the first medical image, the second medical image, and the third medical image, and calculated difference between the first medical image, the second medical image, and the third medical image, a machine learning model to predict anatomical changes to at least one structure of the patient for at least one forecasted treatment fraction; and transmit the prediction of anatomical changes to a radiotherapy treatment planning computer model, whereby when the radiotherapy treatment planning computer model determines that at least one structure of the patient is being underdosed or overdosed, the radiotherapy treatment planning computer model generates a second radiotherapy treatment plan for the patient.

The artificial intelligence model may be a convolutional long short-term memory model. The artificial intelligence model may be trained on a dataset comprising simulated computed tomography imaging approaches and simulated cone-beam computed tomography imaging approaches for previously treated patients. At least one of the computer model or the machine learning model may further ingest at least one treatment attribute. The machine learning model may further ingest an attribute corresponding to patient positioning. The machine learning model may further ingest an attribute corresponding to a physiological regression.

BRIEF DESCRIPTION OF THE DRAWINGS

Non-limiting embodiments of the present disclosure are described by way of example with reference to the accompanying figures, which are schematic and are not intended to be drawn to scale. Unless indicated as representing the background art, the figures represent aspects of the disclosure.

DETAILED DESCRIPTION

Figure 1:
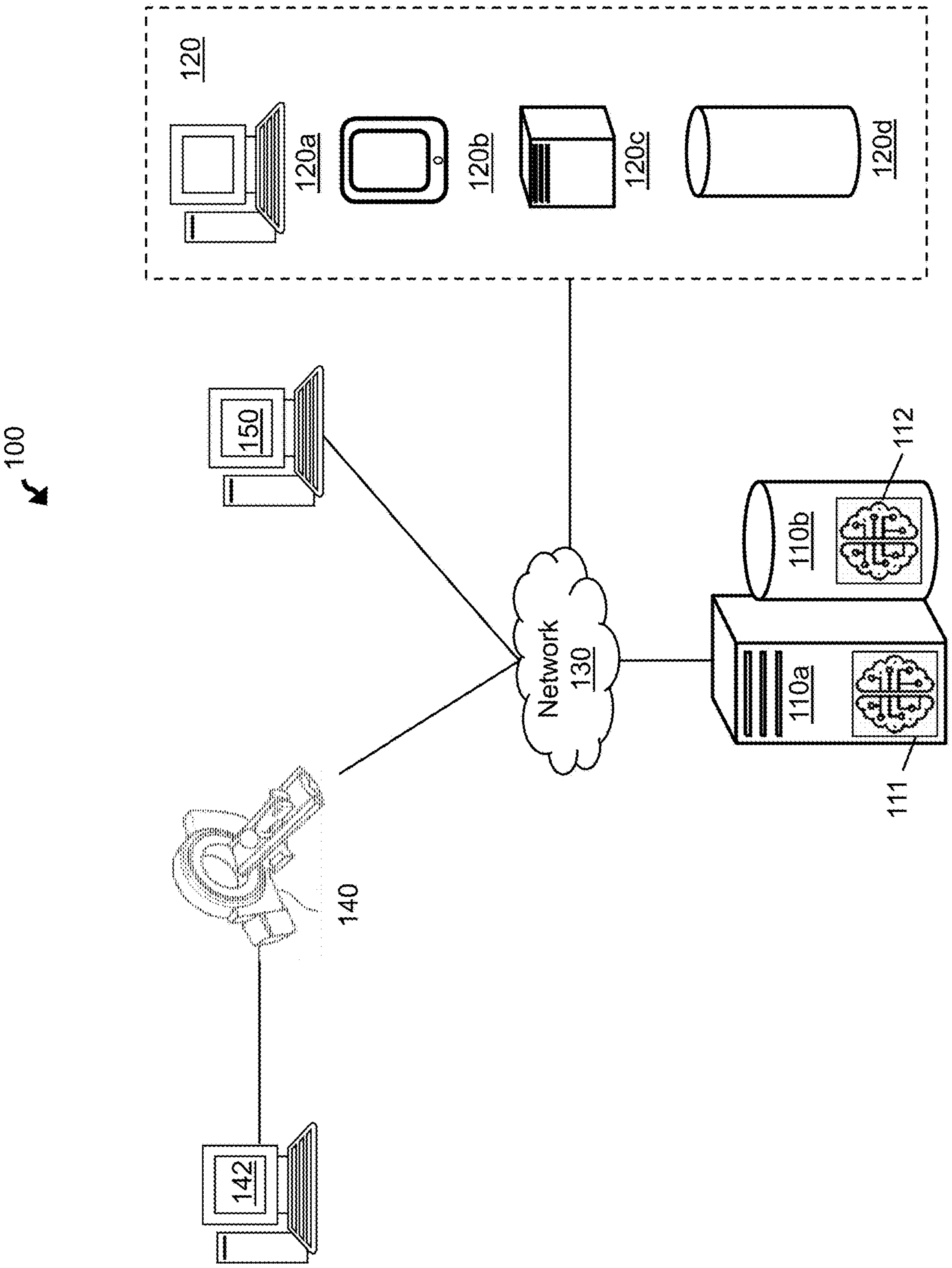
FIG. 1 illustrates components of an AI-enabled RTTP generation system, according to an embodiment.

Reference will now be made to the illustrative embodiments depicted in the drawings, and specific language will be used herein to describe the same. It will nevertheless be understood that no limitation of the scope of the claims or this disclosure is thereby intended. Alterations and further modifications of the inventive features illustrated herein, and additional applications of the principles of the subject matter illustrated herein that would occur to one skilled in the relevant art and having possession of this disclosure, are to be considered within the scope of the subject matter disclosed herein. Other embodiments may be used and/or other changes may be made without departing from the spirit or scope of the present disclosure. The illustrative embodiments described in the detailed description are not meant to be limiting to the subject matter presented.

FIG. 1 illustrates components of an AI-enabled RTTP generation system (system 100), according to an embodiment. The system 100 may include an analytics server 110*a*, system database 110*b*, clinical model analysis computer model 111, end-user devices 120*a-d* (collectively end-user devices 120), and an administrator computing device 150. Various components depicted in FIG. 1 may belong to a radiation therapy clinic at which patients may receive radiation therapy treatment via one or more radiation therapy machines (e.g., medical device 140) in the clinic. The above-mentioned components may be connected through a network 130. Examples of the network 130 may include, but are not limited to, private or public LAN, WLAN, MAN, WAN, and the Internet. The network 130 may employ wired and/or wireless communications according to one or more standards and/or via one or more transport mediums.

The communication over the network 130 may be performed in accordance with various communication protocols such as Transmission Control Protocol and Internet Protocol (TCP/IP), User Datagram Protocol (UDP), and IEEE communication protocols. In one example, the network 130 may include wireless communications according to Bluetooth specification sets or another standard or proprietary wireless communication protocol. In another example, the network 130 may also include communications over a cellular network, such as a GSM (Global System for Mobile Communications), CDMA (Code Division Multiple Access), or EDGE (Enhanced Data for Global Evolution) network.

The system 100 is not confined to the components described herein and may include additional or other components, not shown for brevity, which is to be considered within the scope of the embodiments described herein.

The analytics server 110*a* may generate and display an electronic platform configured to use various computer models 111-112 to identify attributes of an RTTP for a patient's treatment. The electronic platform may include a graphical user interface (GUI) displayed on the end-user devices 120 and/or the administrator computing device 150. An example of the electronic platform generated and hosted by the analytics server 110*a* may be a web-based application or a website configured to be displayed on different types of electronic devices, such as mobile devices, tablets, personal computers, and the like.

In a non-limiting example, a physician operating the physician device 120*b* may access the platform, input patient attributes, characteristics, and other data, and further instruct the analytics server 110*a* to generate an RTTP (including the beam angle, physiological regression, patient positioning, dose constraints, treatment schedule, etc.). Additionally or alternatively, the analytics server 110*a* may optimize only one particular attribute of the RTTP (e.g., optimize beam angle or dose constraints delivered to the tumor and surrounding healthy organs).

The analytics server 110*a* may recommend the RTTP (e.g., beam angles and other radiation parameters and/or treatment plan attributes) used for proton radiation, photon radiation, and electron radiation. In particular, analytics server 110*a* may utilize the methods and systems described herein to execute the clinical model analysis computer 111 for identifying cost values or predicting anatomical changes in the patient's anatomy that can ultimately be used (e.g., by the plan optimizer model 112) to evaluate and re-evaluate the RTTP. Further, the analytics server 110*a* may transmit the beam angles and other radiation parameters and/or treatment plan attributes to one or more other servers. Additionally, or alternatively, the analytics server 110*a* (or another server) may adjust the configuration of one or more devices (e.g., the medical device 140) based on the systematic changes observed in the patient's anatomy from one treatment fraction to another. For instance, the RTTP may be directly sent to the medical device 140 and/or the computer 142 that functionally controls the medical device 140 used in the treatment plan.

The medical device 140 may be any medical device used in the radiation therapy treatment of a patient (such as a CT scan machine, radiation therapy machine (e.g., a linear accelerator, particle accelerator (including circular accelerators), or cobalt machine)). The medical device 140 may also include an imaging device capable of emitting radiation such that the medical device 140 may obtain images according to various methods to accurately image the internal anatomical structure of a patient. For instance, the medical device 140 may include a rotating system (e.g., a static or rotating multi-view system). A non-limiting example of a multi-view system may include stereo systems (e.g., two systems arranged orthogonally).

The analytics server 110*a* may host a website accessible to users operating any of the electronic devices described herein (e.g., end-users or medical professionals), where the content presented via the various webpages may be controlled based upon each particular user's role or viewing permissions. The analytics server 110*a* may be any computing device comprising a processor and non-transitory, machine-readable storage capable of executing the various tasks and processes described herein. The analytics server 110*a* may employ various processors, such as central processing units (CPU) and graphics processing units (GPU), among others. Non-limiting examples of such computing devices may include workstation computers, laptop computers, server computers, and the like. While the system 100 includes a single analytics server 110*a*, the analytics server 110*a* may include any number of computing devices operating in a distributed computing environment, such as a cloud environment.

The analytics server 110*a* may execute software applications configured to display the electronic platform (e.g., host a website), which may generate and serve various webpages to each end-user devices 120. Different users may use the website to view and/or interact with the recommended (optimized) results. Different servers, such as a clinic server 120*c*, may also use the recommended results in downstream processing.

The analytics server 110*a* may be configured to require user authentication based upon a set of user authorization credentials (e.g., username, password, biometrics, cryptographic certificate, and the like). The analytics server 110*a* may access the system database 110*b* configured to store user credentials, which the analytics server 110*a* may be configured to reference in order to determine whether a set of entered credentials (purportedly identifying the user) match an appropriate set of credentials that authenticate the user.

The analytics server 110*a* may generate and host webpages based upon a particular user's role within the system 100. In such implementations, the user's role may be defined by data fields and input fields in user records stored in the system database 110*b*. The analytics server 110*a* may authenticate the user and may identify the user's role by executing an access directory protocol (e.g., LDAP). The analytics server 110*a* may generate webpage content that is customized according to the user's role as defined by the user record in the system database 110*b*.

The analytics server 110*a* may receive various clinical objectives, patient data, and treatment data from the end-user devices 120. For instance, a physician may access the platform provided by the analytics server 110*a* using a physician device 120*b*. The physician may input various patient attributes and/or clinical objectives using one or more input elements of the platform. The analytics server 110*a* may then execute various methods discussed herein and display an RTTP on the platform.

The end-user devices 120 may be any computing device comprising a processor and a non-transitory machine-readable storage medium capable of performing the various tasks and processes described herein. Non-limiting examples of end-user devices 120 may be a workstation computer, laptop computer, tablet computer, and server computer. During operation, various users may use end-user devices 120 to access the GUI operated by the analytics server 110*a*. Specifically, the end-user devices 120 may include a clinic computer 120*a*, a physician device 120*b*, a clinic server 120*c*, or a clinic database 120*d*.

In order to generate the RTTP, the analytics server 110*a* may then execute various models (e.g., clinical model analysis computer model 111 and/or a plan optimizer model 112) to analyze the retrieved/received data.

The administrator computing device 150 may represent a computing device operated by a system administrator. The administrator computing device 150 may be configured to display beam angles, radiation parameters, and/or other radiation therapy treatment attributes generated by the analytics server 110*a*; monitor the clinical model analysis computer model 111 utilized by the analytics server 110*a* and/or end-user devices 120; review feedback; and/or facilitate training or retraining (calibration) of the models 111-112 that are maintained by the analytics server 110*a*.

The analytics server 110*a* may be in communication (real-time or near real-time) with the medical device 140 (or its computer 142), such that a server/computer hosting the medical device 140 can adjust the medical device 140 based on the RTTP (e.g., beam angles, treatment attributes and/or radiation parameters determined by the analytics server 110*a*). For instance, the radiation therapy machine may adjust the gantry, beam blocking device (e.g., multi-leaf collimator MLC), and couch setup based on dose constraints or optimized beam angles, where the optimized beam angle is an angle of the medical device 140 that emits radiation in a direction of the PTVs. The analytics server 110*a* may transmit instructions to the radiation therapy machines indicating any number or type of radiation parameters and/or treatment attributes to facilitate such adjustments.

The clinical model analysis computer model 111 and/or 112 may represent any collection of algorithmic logic and/or artificial intelligence models (e.g., using various machine learning techniques). In some embodiments, the clinical model analysis computer model 111 and/or 112 may include a convolutional long short-term memory (LSTM) model. The clinical model analysis computer model 111 may include various algorithms to identify a cost value for an RTTP based on patient data and/or treatment attributes and how they would likely cause a secondary and/or long-term effect (e.g., health problem). In some embodiments, the clinical model analysis computer model 111 may include various algorithms that process a series of treatment fraction images and predict anatomical changes in at least one structure of the patient for a forecasted treatment fraction. Using the clinical model analysis computer model 111, the analytics server 110*a* may execute the plan optimizer model 112. For instance, the analytics server 110*a* may execute the models in conjunction with each other and then revise one or more configuration or treatment parameters of the plan optimizer 112. In some embodiments, the analytics server 110*a* may execute the plan optimizer model 112 in conjunction with other models, such as the LSTM model, to revise the initial treatment plan in response to determining that at least one structure of the patient is being underdosed or overdosed. As a result, the efficiencies discussed herein can be achieved without revising the plan optimizer 112 itself. For instance, the clinical model analysis computer model 111 can be executed independently and used in conjunction with an existing plan optimizer. Therefore, the plan optimizer (or the system infrastructure) can be retrofitted using the methods and systems discussed herein. This minimal interference with existing infrastructure allows for the improvement of a plan optimizer without the need to revise its source code.

In some embodiments, the analytics server 110*a* may collect patient data from various sources not shown in FIG. 1. For instance, the analytics server 110*a* may monitor and collect patient and treatment attributes associated with previously-treated radiotherapy patients to include in a training dataset. This may include data on the number of treatment fractions undergone by each patient. Additionally, or alternatively, the analytics server 110*a* may collect/aggregate other patient data (e.g., data associated with how a set of patients or clinical participants received their respective radiotherapy treatment). Using the collected data, the analytics server 110*a* may generate a training dataset with which the analytics server 110*a* can train the clinical model analysis computer model 111, including the LSTM model. As a result, the clinical model analysis computer model 111 may be used to limit the search space used by the plan optimizer 112.

Figure 2:
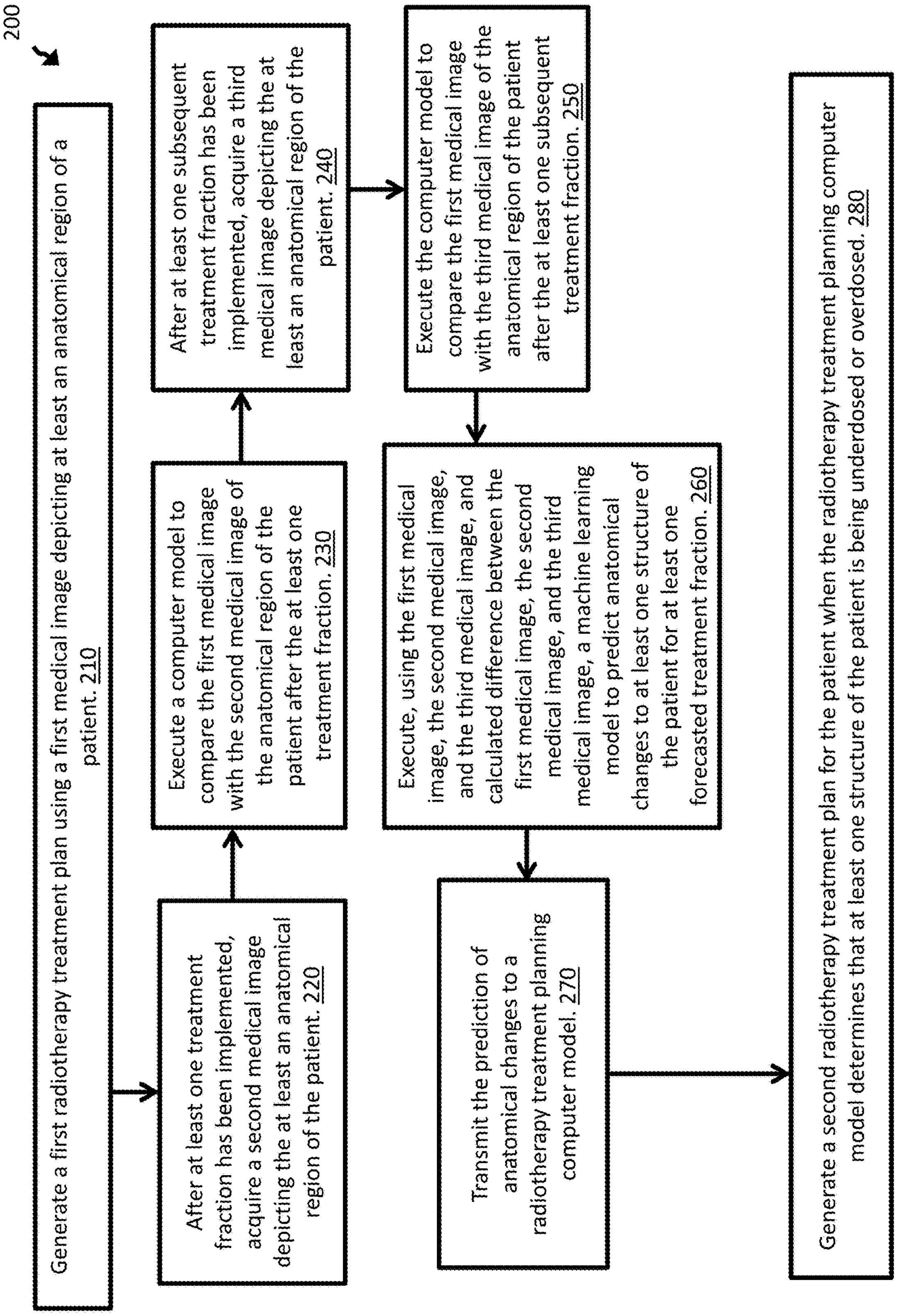
FIG. 2 illustrates a flow diagram of a process executed in an AI-enabled RTTP generation system, according to an embodiment.

FIG. 2 illustrates a flow diagram of a process executed in an AI-enabled RTTP generation system, according to an embodiment. The method 200 includes steps 210-280. However, other embodiments may include additional or alternative execution steps or may omit one or more steps altogether. The method 200 describes how an AI model may be trained and then executed, such that it can predict systematic changes in the patient's anatomy from one treatment fraction to another. One or more steps of method 200 may be executed by any number of computing devices operating in the distributed computing system described in FIG. 1. For instance, a different processor (or even a third-party processor) may train the artificial intelligence model than the processor executing the same artificial intelligence model. Moreover, the artificial intelligence model may be executed in conjunction with a plan optimizer that is being executed for and/or by a third party. Therefore, even though the method 200 is described as being executed/implemented by the analytics server, it is possible that each step of the method 200 is executed for a different entity/processor.

At step 210, the analytics server may generate a first radiotherapy treatment plan (RTTP) using a first medical image depicting at least an anatomical region of a patient. The first radiotherapy treatment plan can be generated by a plan optimizer. The plan optimizer can be computer model (s) or software solution(s) that can run a plurality of simulations with various radiation or treatment parameters and can select, based on the simulation results, an initial set of parameters to be used. The first radiotherapy treatment plan may have a plurality of treatment fractions. A treatment fraction may refer to a single dose of radiation administered during the radiotherapy regimen. In some embodiments, a fraction of treatment may refer to a treatment session.

Prior to administering any treatment fraction, a first medical image corresponding to a pre-treatment computed tomography (CT) scan may be acquired according to the specifications determined according to the radiotherapy treatment plan. The pre-treatment CT scan may represent a detailed and accurate model of the patient's anatomy, mirroring precisely how the anatomy would appear during the actual treatment. The pre-treatment CT scan may provide a baseline from which any changes due to treatment fraction can be identified. For instance, the pre-treatment CT scan may provide a visual representation of the patient's anatomy before the commencement of the first treatment fraction. The reference image may be used throughout the patient's treatment course to monitor anatomical changes. In some embodiments, the pre-treatment CT scan may incorporate imaging techniques that may improve the visibility of surrounding organs and tumors to allow for more accurate assessments of tumor size, location, and proximity to surrounding organs.

The analytics server may receive various treatment attributes determined by a treating physician or a clinician for a patient's radiotherapy treatment. These attributes may be determined for the patient based on the patient's treatment and are generally referred to as plan objectives. A non-limiting example of a plan objective may include dose limits, where a treating physician identifies the dosage that needs to be applied to the tumor. The analytics server may receive and/or retrieve (via a platform and/or via querying a database) patient data to generate a treatment plan for the patient. Therefore, as used herein, patient data may refer to any data that is associated with the patient (e.g., the patient's physical data, diagnosis data, and any data inputted by a medical professional). In some embodiments, the analytics server may use different patient identifiers to retrieve the patient data. For instance, the analytics server may query one or more databases to identify medical data associated with the patient. The analytics server may query data associated with the patient's anatomy, such as physical data (e.g., height, weight, and/or body mass index) and/or other health-related data (e.g., blood pressure or other data relevant to receiving radiation therapy treatment). The analytics server may also retrieve data associated with current and/or previous medical treatments received by the patient (e.g., data associated with the patient's previous surgeries).

In some embodiments, the analytics server may process the patient's medical data records to identify the patient attributes needed. For instance, the analytics server may query a database to identify the patient's body mass index (BMI). However, because many medical records are not digitized, the analytics server may not receive the patient's BMI value using simple query techniques. As a result, the analytics server may retrieve the patient's electronic health data and may execute one or more analytical protocols (e.g., natural language processing) to identify the patient's body mass index. In another example, if the analytics server does not receive tumor data (e.g., end-points), the analytics server may execute various image recognition protocols and identify the tumor data.

In some embodiments, the analytics server may receive additional data from one or more medical professionals. For instance, a treating oncologist may access a platform generated/hosted by the analytics server and may add, remove, or revise data associated with a particular patient, such as patient attributes, treatment attributes, tumor attributes, the primary site of treatment, tumor stage, endpoints, whether the primary tumor has been extended, and the like. Because tumor staging and the end-level attributes are critical pieces of information that affect patient treatment, this information may be inputted by the treating oncologist. In some embodiments, an AI model (e.g., a separate AI model that is trained to identify tumor information) may identify this information, and the treating oncologist may deny, approve, or revise the predicted results. In another example, the treating oncologist may specifically indicate whether the treatment should be unilateral or bilateral.

Another example of the plan objective and/or patient data/attributes may include specific tumor locations. More specifically, this data may indicate the primary tumor location with respect to the patient's centerline. This data may be inputted by the treating oncologist or may be analyzed using various image recognition or segmentation methods executed on the patient's medical images. In some embodiments, this information may be predicted using the AI model if it is not inputted by the treating oncologist (or otherwise received by the analytics server). Another patient attribute may indicate whether and how close the tumor volume (e.g., planning target volume) is to other non-diseased organs (e.g., organs at risk). For instance, a tumor to be eradicated may be millimeters away from another organ. This information may change field geometry (generated by the optimizer), as other organs must be avoided.

Based on the patient's data analysis and optimization process, the analytics server may generate the RTTP, for example, via the plan optimizer (or a radiotherapy treatment planning computer model) that may specify the number, angles, and shapes of the radiation beams used to deliver the treatment, the total dose of radiation to be delivered, and the fractionation schedule (number of treatment sessions and dose per session), among others.

At step 220, after at least one treatment fraction has been implemented, the analytics server may acquire a second medical image depicting at least an anatomical region of the patient. The second medical image may refer to cone-beam CT (CBCT) scans, periodic CT scans, positron emission tomography (PET) scans, and magnetic resonance imaging (MRI), among others. The CBCT scan may be acquired to provide a 3D view of the patient's anatomy. Patients undergoing RT often experience weight loss and tumor shrinkage, leading to changes in their anatomy (e.g., also known as physiological regression). Since the RT treatment plan relies on the initial patient anatomy, the physiological regression can cause underdosing of the tumor and overdosing of surrounding organs. In some cases, during treatment, patients are positioned based on markers or bony anatomy. However, tumor and organ deformation can occur, and even slight positioning errors can result in underdosing the tumor and overdosing the organs. In some embodiments, the post-treatment image may be used to monitor tumor shrinkage or weight loss. In some embodiments, the post-treatment image may be used to verify if the patient's positioning during treatment delivery matches the planned position used for treatment planning.

At step 230, the analytics server may execute a computer model to compare the first medical image with the second medical image of the anatomical region of the patient after the at least one treatment fraction. The analytics server may cause the computer model(s) or software solution(s) to perform deformable image registration based on deformable image registration algorithms. The deformable image registration algorithms may be predefined. For instance, the computer model may be configured to align the two images despite potential anatomical changes. The deformable image registration algorithms may account for the deformations (e.g., anatomical variations in the patient's anatomy) by warping the CBCT scan (second medical image) to match the reference pre-treatment CT scan (first medical image) as closely as possible, incorporating anatomical information to achieve more accurate alignment.

In some embodiments, the comparison or image registration process may include considering landmarks such as bones or organ shapes to guide the warping process. In some embodiments, the computer model may adjust the warping of the CBCT scan based on intensity comparisons (e.g., brightness of corresponding pixels) between the CBCT scan and the reference CT scan. The computer model may process the medical image data to monitor specific anatomical structures within the aligned medical images, such as the position and shape of relevant organs and the gross tumor volume, which may refer to the visible portion of the tumor identified for treatment. In some embodiments, the computer model may be configured to track changes in organ positions, tumor shrinkage, and potentially other anatomical shifts.

At step 240, after at least one subsequent treatment fraction has been implemented, the analytics server may acquire a third medical image depicting the at least an anatomical region of the patient. The third medical image of the patient's anatomy may be acquired after at least one additional treatment session (a subsequent fraction) has been delivered. The third image can be another CBCT scan acquired during the second treatment fraction. In some embodiments, the third medical image may be acquired using any imaging modality performed after the first treatment fraction. The third medical image may provide data for ongoing treatment evaluation. The third medical image may be used to assess how the patient's anatomy has responded to the therapy thus far, including any changes in tumor size, position, or the condition of surrounding tissues.

At step 250, the analytics server may execute the computer model to compare the first medical image with the third medical image of the anatomical region of the patient after the at least one subsequent treatment fraction. This comparison may occur after at least one subsequent treatment fraction has been administered, allowing for an assessment of changes over an extended treatment period. Similar to step 230, the computer model may employ deformable image registration techniques for aligning images taken at different times during the treatment process, which may not match perfectly due to physiological changes the patient has undergone, such as tumor shrinkage, organ movement, or other anatomical adjustments that may have occurred during the course of treatment. In this example, the computer model can align the pre-treatment CT scan (used as the baseline or first medical image) with the third medical image (second CBCT scan).

By comparing the baseline image with the most recent image, the analytics server, via the computer model, may determine how effectively the tumor and surrounding tissues are responding to the treatment. In some embodiments, the computer model may be configured to compare the previously registered second medical image with the third medical image to provide additional insights by providing a closer, sequential observation of the anatomical changes. In some embodiments, the computer model may be configured to compare the registered second medical image with the registered third medical image, depending on the implementation.

At step 260, the analytics server may execute, using the first medical image, the second medical image, and the third medical image, and calculated difference between the first medical image, the second medical image, and the third medical image, a machine learning model to predict anatomical changes to at least one structure of the patient for at least one forecasted treatment fraction. The forecasted fraction may refer to future sessions of the treatment plan that have not yet been administered.

The machine learning model may include a convolutional long short-term memory (LSTM) model, which is trained to predict certain clinical outcomes. The LSTM model may be trained on various datasets, including those composed of simulated CT imaging approaches and simulated CBCT imaging approaches. In some embodiments, the training dataset may include both types of images as well as any other images from previously treated patients, depending on the implementation. In some embodiments, the input to the LSTM model may include a set of channels describing different (independent) features of the finalized and/or candidate RTTPs generated by the plan optimizer or computer model. Non-limiting examples of the input to the artificial intelligence model may include dose distribution (of the current candidate RTTP, some other similar information such as "2Gy equivalent dose" or "proton-LET," and/or some dose-rate corrected dose distribution trying to capture flash effect), target or organ-at-risk masks, and/or CT or other imaging modalities.

In some embodiments, the training dataset may include data associated with the patient and their specific RTTP. For instance, for each patient, the training dataset may include patient data (e.g., all available data associated with the patient's anatomy, disease, diagnoses, and any other data ingested by the plan optimizer at the time the patient was treated), any data available that was inputted by the patient's treating physician, and/or the patient's RTTP and its attributes. That is, the training dataset may include each patient's information regarding their anatomy and disease, how the patient was diagnosed, how the patient was treated, and how the patient experienced health-related issues and a corresponding timeline. Using this training dataset, the analytics server may train the LSTM model, such that the machine learning model can ingest data associated with a new patient and the new patient's RTTP to predict the likelihood of a health-related issue occurring. The training may be conducted using a supervised, unsupervised, or semi-supervised manner.

In some embodiments, different arrangements of images can be fed into the LSTM model to enhance its processing capabilities. In some embodiments, the input channels may need to be in a certain spatial resolution and size. Accordingly, the LSTM model can include a component that checks that the dimensionality and resolution of the input data, such that the image can be ingested by the LSTM model. The LSTM model may process or compare the pre-treatment CT scan and the second fraction image to understand long-term changes. In some embodiments, the LSTM model may process the differences sequentially (e.g., from first to second and second to third) to capture more granular shifts in anatomy.

In some embodiments, the LSTM model may be configured to simultaneously analyze all three images (e.g., the first medical image, the second fraction image, and the third medical image) and/or registered images (e.g., the calculated difference between any sequence of images) to provide a comprehensive overview of the anatomical changes over the entire course of the treatment. The LSTM model can be configured to learn from sequences, such as the series of CBCT images acquired throughout the initial treatment fractions. By analyzing this sequence, the LSTM model may identify patterns and trends in anatomical changes observed in past CBCT scans and, based on these patterns and the current state (the most recent CBCT image), predict how the anatomical structures may change in future treatment fractions.

In some embodiments, the treatment plan may involve conducting a predefined number of treatment fraction images. In some embodiments, the analytics server can be configured to execute the LSTM model in response to specific triggers defined within the treatment plan. For instance, the analytics server may execute the LSTM model processing once the predefined number of treatment fractions has been completed. For instance, the LSTM model may be programmed to execute an action after six treatment fractions have been implemented, although this threshold can be set to any positive integer as per the clinical requirements.

After a predefined number of treatment fraction images have been implemented, the analytics server may execute the LSTM model to predict anatomical changes to at least one structure of the patient for at least one forecasted treatment fraction. The LSTM model can be configured to focus on specific aspects of relevant organs surrounding the tumor (organs at risk) that may be affected by the radiation treatment and the target volume. In some embodiments, the LSTM model may predict systematic changes such as positional changes in organs due to factors like tumor shrinkage, which may create more space for surrounding organs to move or treatment-related effects like tissue swelling or weight loss that could cause organ displacement.

In some embodiments, the LSTM model may predict shape alterations in organs due to radiation-induced deformation or normal anatomical variations during body movements. In some embodiments, the LSTM model may be configured to focus on predicting the extent of tumor shrinkage in response to radiation treatment. The LSTM model may predict other potential changes in the target volume, such as deformation due to treatment effects or internal changes within the tumor, based on historical data and treatment response patterns.

In some systems, the LSTM model may be configured to consider additional information, such as treatment attributes. The treatment attributes may include errors related to patient positioning, where there are deviations from the planned positioning during treatment delivery, and physiological regression, which encompasses unexpected changes in the patient's body due to factors such as weight loss or organ movement. The LSTM model may distinguish and separate treatment attributes from anatomical changes. By identifying and separating out the treatment attributes, the LSTM model may enhance the accuracy of the predictions to account for intended treatment trajectories and unforeseen changes in the patient's anatomy.

At step 270, the analytics server may transmit the prediction of anatomical changes to a radiotherapy treatment planning computer model. In some embodiments, the RTTP computer model may utilize neural network models (plan optimizers, or other machine learning models) to automatically segment organs and tumors from medical images, suggest appropriate treatment modalities, and determine optimal field geometry settings for radiation beams. In some embodiments, the RTTP computer model can identify that at least one structure (e.g., organs or tumors) of the patient experiences deviations (e.g., underdose or overdose) from the planned radiation dose. The deviation may refer to variations exceeding acceptable thresholds that may harm healthy organs or compromise tumor control, as defined by the treatment plan. For instance, if a tumor receives less radiation than planned, it may not shrink as expected.

In some embodiments, excessive radiation can cause inflammation of healthy organs. In some embodiments, patients may be evaluated against set schemas regarding side effects and/or known health-related issues. Non-limiting examples of these health-related issues may include xerostomia; headaches; hair loss; nausea; vomiting; extreme tiredness (fatigue); hearing loss or impairment; skin and/or scalp issues (changes), trouble with memory and/or speech, sore skin, diarrhea, fertility issues, and the like. When a health-related problem is identified, human reviewers (or sometimes using a processor that uses pre-set rules), can quantify the health-related problem, such that the quantified health-related problem and its corresponding category can be included within the training dataset for the computer models or machine learning models. Moreover, the health-related problem may include the development of secondary cancer. The training dataset may also include a timeline associated with each health-related problem.

In some embodiments, the RTTP computer model may predict a cost value that corresponds to the high-level utility of certain predicted probabilities, such as the probability of one or more side effects of other medical issues occurring. The cost value may correspond to a likelihood of the initial RTTP causing a health-related issue, such as long-term side effects or other health issues discussed herein. In some embodiments, the LSTM model may be configured to calculate the cost value that can be directly used by the RTTP computer model. Additionally, or alternatively, the LSTM model may generate one or more scores that can then be used to calculate the cost value by the RTTP computer model. For instance, the values predicted by the LSTM model may be transformed (e.g., using other algorithms) to the cost value. Accordingly, the LSTM model can be trained to predict one or more attributes, which can then be converted into a cost value that is used by the RTTP computer model.

Based on the predictions, the RTTP computer model may recommend and/or generate a second radiotherapy treatment plan. For instance, in situations where significant and unexpected anatomical changes are predicted, a treatment replan may be generated. In some embodiments, the treatment replan may be automated, where the RTTP computer model automatically generates a new plan based on the predicted changes. In some embodiments, the treatment replan may include medical professionals reviewing available data, including CBCT scans and dose delivery information, to recalibrate or adjust doses (e.g., via a dose summation algorithm) for optimal treatment delivery despite the anatomical changes. For instance, the secondary dose deposition in the second treatment plan may differ from the initial dose deposition specified in the first treatment plan.

Figure 3:
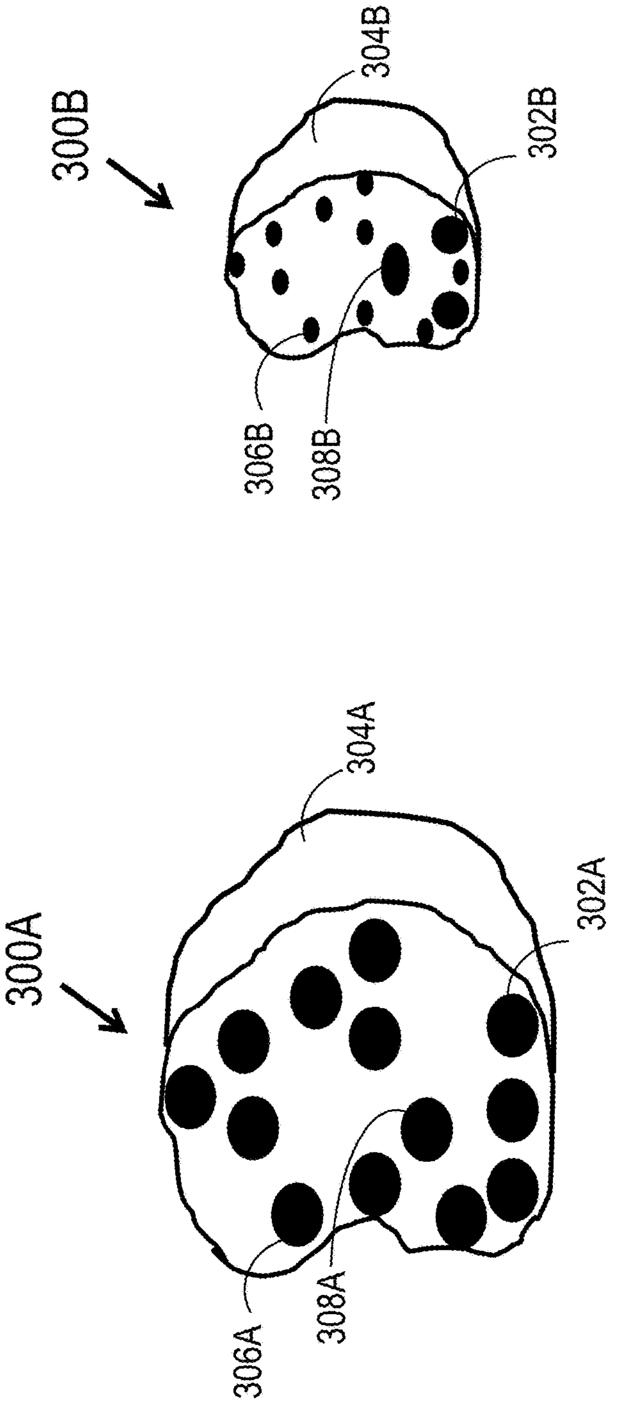
FIG. 3 illustrates example pre-treatment and post-treatment fraction images, according to an embodiment.

Referring now to FIG. 3, depicted is a cross-sectional view of a tumor volume and its surrounding organs within a patient's body, illustrating pre-treatment fraction image 300A and post-treatment fraction image 300B (e.g., after at least one fraction of treatment). The treatment fraction images may be used to determine the need for replanning in radiation treatment, as explained in connection with FIG. 2. The pre-treatment fraction image 300A shows larger tumor lesions 306A, 308A (depicted as black dots). In some embodiments, the black dots (representing different tumor lesions) may be used to assess whether the initially targeted areas still align with the size and shape of the tumor, as determined during the initial treatment plan. In some embodiments, the tumor lesions may be used to indicate regions targeted for intense radiation focus.

The post-treatment image 300B shows a reduced tumor volume for some of the tumor lesions (306A versus 306B). In some embodiments, the tumor lesions (308A versus 308B) may exhibit a shape change and/or, sometimes, a reduction in size. In some embodiments, a tumor lesion may not change in size or shape (e.g., tumor lesion 302A versus 302B). The reduction in tumor size and/or shape can lead to a misalignment between the planned high-dose regions and the tumor's boundaries. Such misalignment may result in underdosing some parts of the tumor, potentially compromising the treatment's effectiveness.

Adjacent to the tumor lesions in both images are organs at risk (304A in the pre-treatment fraction image and 304B in the post-treatment fraction image). The proximity of the OARs to the tumor lesions being treated may be another consideration for revising the treatment plan. For instance, as treatment progresses, factors such as weight loss or physiological changes in the patient may cause both the tumor and nearby organs to shift. As shown in the post-treatment fraction image 300B, the tumor lesions, which indicate areas targeted for intense radiation focus, are extending toward the surrounding organs 304B. This movement may place the organ at risk closer to the high-dose zones intended for the tumor, increasing the likelihood of the organ receiving unintended radiation exposure. Such misalignment may result in overdosing the surrounding organs. The extension of tumor volume toward the surrounding organs can present a need for treatment replanning and adjustment of radiation beams.

Figure 4:
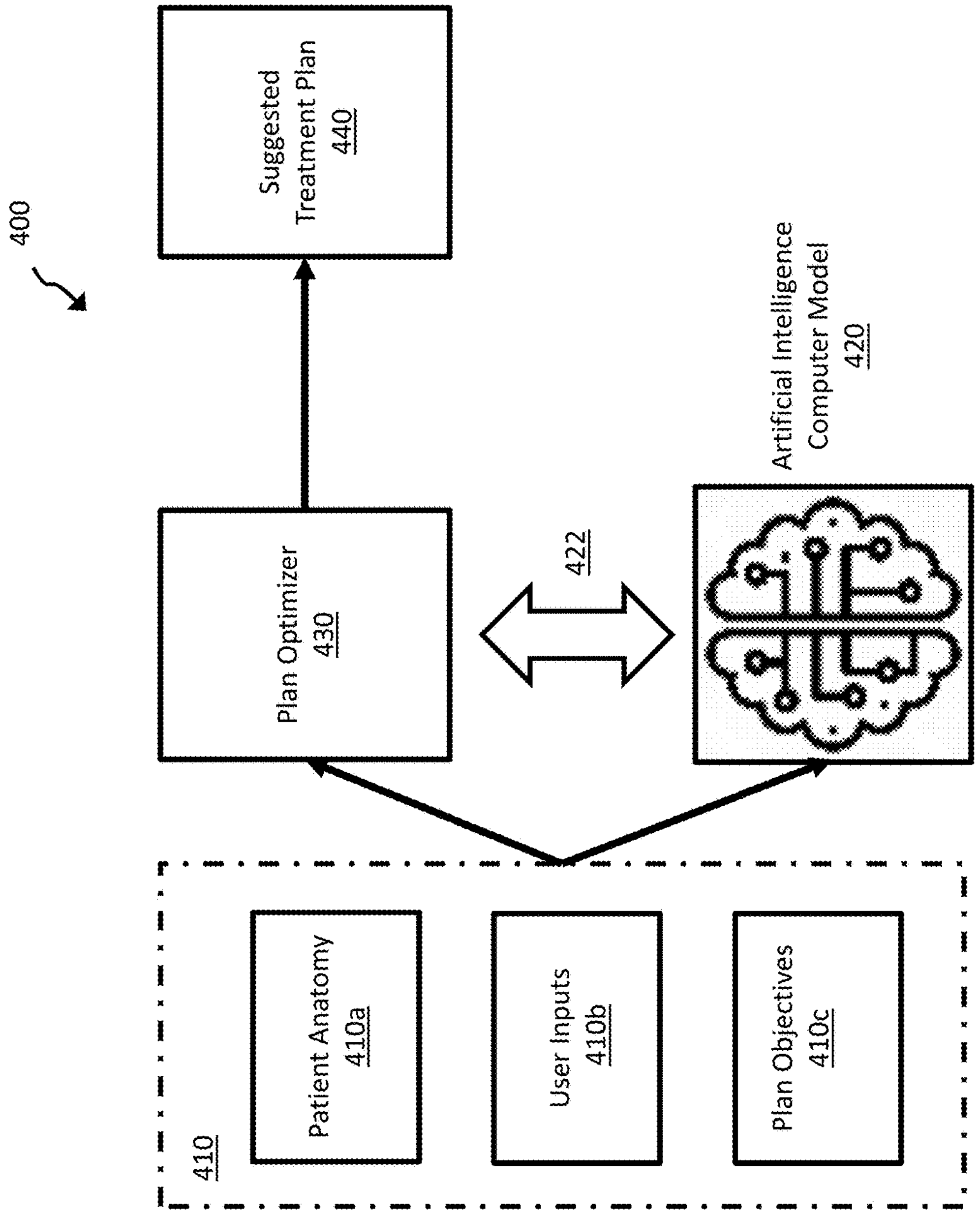
FIG. 4 illustrates different flow diagrams of different processes executed in an AI-enabled RTTP generation system to predict systematic changes in a patient's anatomy from one treatment fraction to another, according to an embodiment.

Referring now to FIG. 4, a non-limiting visual example of a workflow utilizing the methods and systems described herein is illustrated. In this non-limiting example 400, the analytics server provides plan objectives 410*c*, patient anatomy 410*a*, user inputs 410*b*, and other data that may be needed to generate an RTTP (collectively patient data 410) to the plan optimizer 430 to generate a suggested RTTP that is optimized for a patient and their treatment. The analytics server may also transmit the data 410 to the artificial intelligence computer model 420. As a result, the artificial intelligence computer model 420 (such as the LSTM model) may transmit predicted systematic changes in a patient's anatomy from one treatment fraction to another to the plan optimizer 430, where the two models can iteratively work together to generate and/or revise the suggested treatment plan 440.

The analytics server may first collect patient data 410. The patient data may include patient anatomy data 410*a* (e.g., medical images, PTVs, OARs), and user inputs 410*b* (clinical objectives or rules received via a user interface from a treating oncologist, such as tumor data, PTV identification, and the like). Other non-limiting examples of clinical goals may include dosimetric goodness function, robustness metrics, biological effects of radiation, metrics of linear energy transfer, and the like. The patient data 410 may also include rules 410*c* for the patient's treatment (e.g., clinical/treatment objectives or criteria identified by the medical professionals or any other special treatments required by the medical professionals).

In some configurations, the analytics server may access a patient's internal/external file and retrieve/extract the needed patient data 410. The analytics server may then execute an artificial intelligence computer model 420 to identify a cost function for a candidate RTTP for the patient using the patient data 410. The results generated via the artificial intelligence computer model 420 may be ingested by the plan optimizer 430. The plan optimizer 430 may be a treatment planning and/or monitoring software solution. The plan optimizer 430 may analyze various factors associated with the patient and the patient's treatment to generate and optimize an RTTP for the patient (e.g., field geometry, treatment modality, and radiation and/or treatment parameters needed to treat the patient).

One of the factors considered by the plan optimizer 430 may be the cost value calculated by the artificial intelligence computer model 420. The plan optimizer 430 may iteratively revise the patient's RTTP, wherein the plan optimizer 430 iteratively revises different attributes of the RTTP (e.g., dose constraints delivered to the planning target volume and organs at risk, field geometry, etc.). In some configurations, the plan optimizer 430 may transmit new treatment plan data back to the artificial intelligence model 420, whereby the dose calculation sector model 420 can recalculate/re-predict the cost value based on the revised treatment data generated by the plan optimizer (iteration 422). The plan optimizer 430 and the artificial intelligence model 420 may repeat iteration 422 until the patient's RTTP is optimized/finalized.

When the plan optimizer 430 completes the patient's RTTP, the plan optimizer 430 may transmit the suggested treatment plan 440 to one or more electronic devices where a user (e.g., clinician) can review the suggested plan. For instance, the suggested treatment plan 440 (or any attributes predicted by the dose calculation sector model 420) may be displayed on a computer of a clinic where a radiation therapy technician or a treating oncologist can review the data.

The various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of this disclosure or the claims.

Embodiments implemented in computer software may be implemented in software, firmware, middleware, microcode, hardware description languages, or any combination thereof. A code segment or machine-executable instructions may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, etc.

The actual software code or specialized control hardware used to implement these systems and methods is not limiting of the claimed features or this disclosure. Thus, the operation and behavior of the systems and methods were described without reference to the specific software code being understood that software and control hardware can be designed to implement the systems and methods based on the description herein.

When implemented in software, the functions may be stored as one or more instructions or codes on a non-transitory computer-readable or processor-readable storage medium. The steps of a method or algorithm disclosed herein may be embodied in a processor-executable software module, which may reside on a computer-readable or processor-readable storage medium. A non-transitory computer-readable or processor-readable media includes both computer storage media and tangible storage media that facilitate the transfer of a computer program from one place to another. A non-transitory processor-readable storage media may be any available media that may be accessed by a computer. By way of example, and not limitation, such non-transitory processor-readable media may comprise RAM, ROM, EEPROM, CD-ROM or other optical disk storage, magnetic disk storage or other magnetic storage devices, or any other tangible storage medium that may be used to store desired program code in the form of instructions or data structures and that may be accessed by a computer or processor. Disk and disc, as used herein, include compact disc (CD), laser disc, optical disc, digital versatile disc (DVD), floppy disk, and Blu-ray disc where disks usually reproduce data magnetically, while discs reproduce data optically with lasers. Combinations of the above should also be included within the scope of computer-readable media. Additionally, the operations of a method or algorithm may reside as one or any combination or set of codes and/or instructions on a non-transitory processor-readable medium and/or computer-readable medium, which may be incorporated into a computer program product.

The preceding description of the disclosed embodiments is provided to enable any person skilled in the art to make or use the embodiments described herein and variations thereof. Various modifications to these embodiments will be readily apparent to those skilled in the art, and the principles defined herein may be applied to other embodiments without departing from the spirit or scope of the subject matter disclosed herein. Thus, the present disclosure is not intended to be limited to the embodiments shown herein but is to be accorded the widest scope consistent with the following claims and the principles and novel features disclosed herein.

While various aspects and embodiments have been disclosed, other aspects and embodiments are contemplated. The various aspects and embodiments disclosed are for purposes of illustration and are not intended to be limiting, with the true scope and spirit being indicated by the following claims.

What we claim is:

1. A method for replanning radiotherapy treatment, the method comprising:

generating, by at least one processor, a first radiotherapy treatment plan using a first medical image depicting an anatomical region of a patient, the first radiotherapy treatment plan having a plurality of treatment fractions;

after at least one treatment fraction has been implemented, acquiring, by the at least one processor, a second medical image depicting the anatomical region of the patient;

executing, by the at least one processor, a computer model to compare the first medical image with the second medical image of the anatomical region of the patient after the at least one treatment fraction;

after at least one subsequent treatment fraction has been implemented, acquiring, by the at least one processor, a third medical image depicting the anatomical region of the patient;

executing, by the at least one processor, the computer model to compare the first medical image with the third medical image of the anatomical region of the patient after the at least one subsequent treatment fraction;

executing, by the at least one processor using the first medical image, the second medical image, and the third medical image, and calculated difference between the first medical image, the second medical image, and the third medical image, a machine learning model to predict anatomical changes to at least one structure of the patient for at least one forecasted treatment fraction; and transmitting, by the at least one processor, the prediction of anatomical changes to a radiotherapy treatment planning computer model, whereby when the radiotherapy treatment planning computer model determines that at least one structure of the patient is being underdosed or overdosed, the radiotherapy treatment planning computer model generates a second radiotherapy treatment plan for the patient.

2. The method of claim 1, wherein the artificial intelligence model is a convolutional long short-term memory model.

3. The method of claim 1, wherein the artificial intelligence model is trained on a dataset comprising simulated computed tomography images and simulated cone-beam computed tomography images for previously treated patients.

4. The method of claim 1, wherein at least one of the computer model or the machine learning model further ingests at least one treatment attribute.

5. The method of claim 1, wherein the machine learning model further ingests an attribute corresponding to patient positioning.

6. The method of claim 1, wherein the machine learning model further ingests an attribute corresponding to a physiological regression.

7. The method of claim 1, wherein the second radiotherapy treatment plan includes a secondary dose deposition for the at least one structure that is different than a dose deposition of a first dose deposition of the first radiotherapy treatment plan.

8. A system comprising:

one or more processors configured to:

generate a first radiotherapy treatment plan using a first medical image depicting an anatomical region of a patient, the first radiotherapy treatment plan having a plurality of treatment fractions;

after at least one treatment fraction has been implemented, acquire a second medical image depicting the anatomical region of the patient;

execute a computer model to compare the first medical image with the second medical image of the anatomical region of the patient after the at least one treatment fraction;

after at least one subsequent treatment fraction has been implemented, acquire a third medical image depicting the anatomical region of the patient;

execute the computer model to compare the first medical image with the third medical image of the anatomical region of the patient after the at least one subsequent treatment fraction;

execute, using the first medical image, the second medical image, and the third medical image, and calculated difference between the first medical image, the second medical image, and the third medical image, a machine learning model to predict anatomical changes to at least one structure of the patient for at least one forecasted treatment fraction; and transmit the prediction of anatomical changes to a radiotherapy treatment planning computer model, whereby when the radiotherapy treatment planning computer model determines that at least one structure of the patient is being underdosed or overdosed, the radiotherapy treatment planning computer model generates a second radiotherapy treatment plan for the patient.

9. The system of claim 8, wherein the artificial intelligence model is a convolutional long short-term memory model.

10. The system of claim 8, wherein the artificial intelligence model is trained on a dataset comprising simulated computed tomography images and simulated cone-beam computed tomography images for previously treated patients.

11. The system of claim 8, wherein at least one of the computer model or the machine learning model further ingests at least one treatment attribute.

12. The system of claim 8, wherein the machine learning model further ingests an attribute corresponding to patient positioning.

13. The system of claim 8, wherein the machine learning model further ingests an attribute corresponding to a physiological regression.

14. The system of claim 8, wherein the second radiotherapy treatment plan includes a secondary dose deposition for the at least one structure that is different than a dose deposition of a first dose deposition of the first radiotherapy treatment plan.

15. A non-transitory machine-readable storage medium having computer-executable instructions stored thereon that, when executed by one or more processors, cause the one or more processors to:

generate a first radiotherapy treatment plan using a first medical image depicting an anatomical region of a patient, the first radiotherapy treatment plan having a plurality of treatment fractions;

after at least one treatment fraction has been implemented, acquire a second medical image depicting the anatomical region of the patient;

execute a computer model to compare the first medical image with the second medical image of the anatomical region of the patient after the at least one treatment fraction;

after at least one subsequent treatment fraction has been implemented, acquire a third medical image depicting the anatomical region of the patient;

execute the computer model to compare the first medical image with the third medical image of the anatomical region of the patient after the at least one subsequent treatment fraction;

execute, using the first medical image, the second medical image, and the third medical image, and calculated difference between the first medical image, the second medical image, and the third medical image, a machine learning model to predict anatomical changes to at least one structure of the patient for at least one forecasted treatment fraction; and transmit the prediction of anatomical changes to a radiotherapy treatment planning computer model, whereby when the radiotherapy treatment planning computer model determines that at least one structure of the patient is being underdosed or overdosed, the radiotherapy treatment planning computer model generates a second radiotherapy treatment plan for the patient.

16. The non-transitory machine-readable storage medium of claim 15, wherein the artificial intelligence model is a convolutional long short-term memory model.

17. The non-transitory machine-readable storage medium of claim 15, wherein the artificial intelligence model is trained on a dataset comprising simulated computed tomography images and simulated cone-beam computed tomography images for previously treated patients.

18. The non-transitory machine-readable storage medium of claim 15, wherein at least one of the computer model or the machine learning model further ingests at least one treatment attribute.

19. The non-transitory machine-readable storage medium of claim 15, wherein the machine learning model further ingests an attribute corresponding to patient positioning.

20. The non-transitory machine-readable storage medium of claim 15, wherein the machine learning model further ingests an attribute corresponding to a physiological regression.

* * * * *